(12) United States Patent
Margus et al.

(10) Patent No.: US 6,955,883 B2
(45) Date of Patent: *Oct. 18, 2005

(54) LIFE SCIENCES BUSINESS SYSTEMS AND METHODS

(75) Inventors: Bradley A. Margus, Boca Raton, FL (US); David R. Cox, Belmont, CA (US); Stephen P. A. Fodor, Palo Alto, CA (US)

(73) Assignee: Perlegen Sciences, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/402,839

(22) Filed: Mar. 26, 2003

(65) Prior Publication Data

US 2004/0091890 A1 May 13, 2004

Related U.S. Application Data (63) Continuation-in-part of application No. 10/107,508, filed on Mar. 26, 2002.

(51) Int. Cl.[7] ................................................. C12Q 1/68
(52) U.S. Cl. ............................... 435/6; 702/19; 702/20; 705/500
(58) Field of Search ............................. 435/6; 705/500; 702/19, 20

(56) References Cited

U.S. PATENT DOCUMENTS

| | | | |
|---|---|---|---|
| 5,525,464 A | 6/1996 | Drmanac et al. | 435/6 |
| 5,972,614 A | 10/1999 | Ruano et al. | 435/6 |

FOREIGN PATENT DOCUMENTS

| | | |
|---|---|---|
| WO | WO 01/01218 A2 | 1/2001 |
| WO | WO 01/04270 A1 | 1/2001 |
| WO | 0180156 | 10/2001 |

OTHER PUBLICATIONS

Jones, Electronic Journal of Biotechnology 3 (2), Aug. 15, 2000).*
Jones, P.B.C., "The Commercialization of Bioinformatics" Electronic Journal of Biotechnology, Aug. 15, 2000, vol. 3, No. 2, pp. 96–113.
Form 10–K filed by Millennium Pharmaceuticals, for the fiscal year ended Dec. 31, 2000.
Form 10–K filed by Applera Corporation, for the fiscal year ended Jun. 30, 2001.
Form 10–K filed by Genzyme Corporation, for the fiscal year ended Dec. 31, 2000.
Form 10–K filed by Human Genome Sciences, Inc., for the fiscal year ended Dec. 31, 2000.
Form 10–K filed by Genaissance Pharmaceuticals, for the fiscal year ended Dec. 31, 2000.
Perlegen Sciences, Inc. Private Placement Memorandum, dated Mar. 30, 2001.
San Jose Mercury News article entitled "Gene Hunters" dated Jan. 21, 2002.
Pail, N., Cox, D.R. et al. "Blocks of Limited Haplotype Diversity Revealed by High–Resolution Scanning of Human Chromosome 21" *Science Magazine* 294, 1719–1723 (2001).
Daly, M.J., Lander, E.S., et al. "High–resolution haplotype structure in the human genome" *Nature Genetics* 29, 229–232 (2001).
Oestreicher, P., "4th Annual Pharmacogenomics and Medicine Lectures" Pharmacogenomics 2 (3), 291–296 (2001).

* cited by examiner

*Primary Examiner*—James Martinell
(74) *Attorney, Agent, or Firm*—Wilson Sonsini Goodrich & Rosati (57) ABSTRACT

Improved life sciences business systems and methods are disclosed. One or more genomes are scanned for single nucleotide polymorphisms. The polymorphisms are assigned to haplotype blocks, and representative SNPs from the haplotype blocks are used in association studies for pharmaceutical and diagnostic developments.

39 Claims, 2 Drawing Sheets

SEQUENCE LISTING

<160> NUMBER OF SEQ ID NOS: 22

<210> SEQ ID NO 1
<211> LENGTH: 23
<212> TYPE: DNA
<213> ORGANISM: artificial sequence
<220> FEATURE:
<223> OTHER INFORMATION: examplary allele with variants

<400> SEQUENCE: 1
cgatctgagc gccccttaac ttc                                              23

<210> SEQ ID NO 2
<211> LENGTH: 23
<212> TYPE: DNA
<213> ORGANISM: artificial sequence
<220> FEATURE:
<223> OTHER INFORMATION: examplary allele with variants

<400> SEQUENCE: 2
tgacctgggc gacctttgac gtg                                              23

<210> SEQ ID NO 3
<211> LENGTH: 23
<212> TYPE: DNA
<213> ORGANISM: artificial sequence
<220> FEATURE:
<223> OTHER INFORMATION: examplary allele with common variants grouped
      into haplotypes

<400> SEQUENCE: 3
cgatctgagc gccccttaac ttc                                              23

<210> SEQ ID NO 4
<211> LENGTH: 23
<212> TYPE: DNA
<213> ORGANISM: artificial sequence
<220> FEATURE:
<223> OTHER INFORMATION: examplary allele with common variants grouped
      into haplotypes

<400> SEQUENCE: 4
tgacctgggc gacctttgac gtg                                              23

<210> SEQ ID NO 5
<211> LENGTH: 23
<212> TYPE: DNA
<213> ORGANISM: artificial sequence
<220> FEATURE:
<223> OTHER INFORMATION: examplary allele from pooled genomes cases

<400> SEQUENCE: 5
tgacctgggc gccccttaac ttc                                              23

<210> SEQ ID NO 6
<211> LENGTH: 23
<212> TYPE: DNA
<213> ORGANISM: artificial sequence
<220> FEATURE:
<223> OTHER INFORMATION: examplary allese from pooled control genomes

```
<400> SEQUENCE: 6
cgatctgagc gacctttgac gtg                                              23

<210> SEQ ID NO 7
<211> LENGTH: 23
<212> TYPE: DNA
<213> ORGANISM: artificial sequence
<220> FEATURE:
<223> OTHER INFORMATION: examplary allele with common variants

<400> SEQUENCE: 7
cgatctgagc gccccttaac ttc                                              23

<210> SEQ ID NO 8
<211> LENGTH: 23
<212> TYPE: DNA
<213> ORGANISM: artificial sequence
<220> FEATURE:
<223> OTHER INFORMATION: examplary allele with common variants

<400> SEQUENCE: 8
tgacctgggc gacctttgac gtg                                              23

<210> SEQ ID NO 9
<211> LENGTH: 23
<212> TYPE: DNA
<213> ORGANISM: artificial sequence
<220> FEATURE:
<223> OTHER INFORMATION: examplary allele from case genomes with common
      variants

<400> SEQUENCE: 9
tgacctgggc gccccttaac gtc                                              23

<210> SEQ ID NO 10
<211> LENGTH: 23
<212> TYPE: DNA
<213> ORGANISM: artificial sequence
<220> FEATURE:
<223> OTHER INFORMATION: examplary allele from control genome with
      common variants

<400> SEQUENCE: 10
cgatctgagc gacctttgac gtg                                              23

<210> SEQ ID NO 11
<211> LENGTH: 23
<212> TYPE: DNA
<213> ORGANISM: artificial sequence
<220> FEATURE:
<223> OTHER INFORMATION: examplary allele with variants correleted to a
      phenotypic state

<400> SEQUENCE: 11
tgacctgggc gccccttaac gtc                                              23

<210> SEQ ID NO 12
<211> LENGTH: 23
<212> TYPE: DNA
<213> ORGANISM: artificial sequence
<220> FEATURE:
<223> OTHER INFORMATION: examplary allele with variants correlated to a
      phenotypic state

<400> SEQUENCE: 12
cgatctgagc gacctttgac gtg                                              23
```

```
<210> SEQ ID NO 13
<211> LENGTH: 23
<212> TYPE: DNA
<213> ORGANISM: artificial sequence
<220> FEATURE:
<223> OTHER INFORMATION: highly correlated variants in case genome

<400> SEQUENCE: 13
tgacctgggc gccccttgac gtc                                            23

<210> SEQ ID NO 14
<211> LENGTH: 23
<212> TYPE: DNA
<213> ORGANISM: artificial sequence
<220> FEATURE:
<223> OTHER INFORMATION: test case sample for highly correlated variants

<400> SEQUENCE: 14
tgacctgtgc gccccttgac gtg                                            23

<210> SEQ ID NO 15
<211> LENGTH: 23
<212> TYPE: DNA
<213> ORGANISM: artificial sequence
<220> FEATURE:
<223> OTHER INFORMATION: test control sample 1 for highly correlated
      variants

<400> SEQUENCE: 15
cgatctgagc gacctttgac gtg                                            23

<210> SEQ ID NO 16
<211> LENGTH: 23
<212> TYPE: DNA
<213> ORGANISM: artificial sequence
<220> FEATURE:
<223> OTHER INFORMATION: test control sample 2 for highly correlated
      variants

<400> SEQUENCE: 16
cgagctgagc gacctttgac gtg                                            23

<210> SEQ ID NO 17
<211> LENGTH: 8
<212> TYPE: DNA
<213> ORGANISM: artificial sequence
<220> FEATURE:
<223> OTHER INFORMATION: examplary haplotype 1

<400> SEQUENCE: 17 cgatctga                                                              8

<210> SEQ ID NO 18
<211> LENGTH: 8
<212> TYPE: DNA
<213> ORGANISM: artificial sequence
<220> FEATURE:
<223> OTHER INFORMATION: examplary haplotype 2

<400> SEQUENCE: 18 tgacctgg                                                              8

<210> SEQ ID NO 19
<211> LENGTH: 23
<212> TYPE: DNA
```

-continued

```
<213> ORGANISM: artificial sequence
<220> FEATURE:
<223> OTHER INFORMATION: examplary case sample 1

<400> SEQUENCE: 19
tgacctgggc gccccttgac gtg                                              23

<210> SEQ ID NO 20
<211> LENGTH: 23
<212> TYPE: DNA
<213> ORGANISM: artificial sequence
<220> FEATURE:
<223> OTHER INFORMATION: examplary case sample 2

<400> SEQUENCE: 20
tgacctgtgc gccccttgac gtg                                              23

<210> SEQ ID NO 21
<211> LENGTH: 23
<212> TYPE: DNA
<213> ORGANISM: artificial sequence
<220> FEATURE:
<223> OTHER INFORMATION: examplary control sample 3

<400> SEQUENCE: 21
cgatctgagc gacctttgac gtg                                              23

<210> SEQ ID NO 22
<211> LENGTH: 23
<212> TYPE: DNA
<213> ORGANISM: artificial sequence
<220> FEATURE:
<223> OTHER INFORMATION: examplary control sample 4

<400> SEQUENCE: 22
cgagctgagc gacctttgac gtg                                              23
```

LIFE SCIENCES BUSINESS SYSTEMS AND METHODS

CROSS REFERENCE TO RELATED APPLICATION

This application is a continuation-in-part of U.S. patent application Ser. No. 10/107,508, filed Mar. 26, 2002, entitled "Pharmaceutical and Diagnostic Business Systems and Methods" which is assigned to the assignee of this application and incorporated herein by reference.

BACKGROUND

Biotechnology/biopharmaceutical companies have found significant commercial success in business methods wherein a biotechnology company partners with a large pharmaceutical company in pursuit of a particular scientific discovery. For example, it is common for biotechnology companies to engage in various discovery processes (e.g. drug "target" discovery processes) whereby they retain downstream intellectual property rights and/or royalty streams. It is also common for biopharmaceutical companies to collaborate with pharmaceutical companies for purposes of drug discovery, wherein the biopharmaceutical companies use one of several methods to identify regions of the genome that play a role in a particular disease.

The DNA that makes up human chromosomes provides the instructions that direct the production of all proteins in the body. These proteins carry out vital functions of life. Variations in DNA are directly related to almost all human diseases, including infectious diseases, cancers, inherited disorders, and autoimmune disorders. Variations in DNA attributing to a phenotypic change, such as a disease or a disorder, may result from a single variation that disrupts the complex interactions of several genes or from any number of mutations within a single gene. For example, Type I and II diabetes have been linked to multiple genes, each with its own pattern of mutations. In contrast, cystic fibrosis can be caused by any one of over 300 different mutations in a single gene. Phenotypic changes may also result from variations in non-coding regions of the genome. For example, a single nucleotide variation in a regulatory region can upregulate or downregulate gene expression or alter gene activity.

Recent technological developments in the field of human genomic have enabled the development of pharmacogenomics, the use of human DNA sequence variability in the development and prescription of drugs. Pharmacogenomics is based on the correlation or association between a given genotype and a resulting phenotype. Since the first correlation study over half-a-century ago linking adverse drug response with amino acid variations in two drug-metabolizing enzymes (plasma cholinesterase and glucose-6-phosphate dehydrogenase), other correlation studies have linked sequence polymorphisms with drug metabolism enzymes, drug targets and drug transporters with compromised levels of drug efficacy or safety.

Pharmacogenomics information is especially useful in clinical settings where correlation information is used to prevent drug toxicities. For example, patients are often screened for genetic differences in the thiopurine methyltransferase gene that cause decreased metabolism of 6-mercaptopurine or azathioprine. However, only a small percentage of observed drug toxicities have been explained adequately by the set of pharmacogenomic markers available to date. In addition, "outlier" individuals, or individuals experiencing unanticipated effects in clinical trials (when administered drugs that have previously been demonstrated to be both safe and efficacious), cause substantial delays in obtaining FDA drug approval and may even cause certain drugs to come off market, though such drugs may be efficacious for a majority of recipients.

The various biotechnological methods used to date to identify target genomic regions include, for example, differential gene expression which essentially looks for differences in gene expression between control and case samples; protein-protein interaction maps which are used to identify drug receptors and their immediate effectors; and mining human sequence databases for sequences similar to known disease-related, pharmacokinetic or pharmacodynamic regulators. In comparison, association studies that correlate and validate genomic regions with a particular phenotypic trait rely on population genetics and robust statistical metrics. Association studies provide a powerful tool to obtain greater amounts of information in a shorter amount of time thus reducing costs of research and development efforts.

Because all humans are 99.9% identical in their genetic makeup, the DNA sequence of any two individuals is nearly identical. Variations between individuals include, for example, deletions or insertions of DNA sequences, variations in the number of repetitive DNA elements in non-coding regions and changes in a single nitrogenous base position, or "single nucleotide polymorphisms" (SNP). It is estimated that there are 3 to 4 million common SNPs that occur in at least 10 percent of people. These common SNPs do not occur independently but are inherited from generation to generation in tandem with other SNPs, forming patterns across the genome. Such groups of SNPs are referred to as SNP haplotype blocks, or simply haplotypes, herein.

Common SNPs are useful for conducting whole-genome association studies. Whole genomes are scanned of individuals, with and without a phenotypic trait (e.g., resistance to a disease, toxicity from a drug), and correlation is made between SNPs of the case group and a particular phenotypic state. Such whole-genome analyses provide a fine degree of genetic mapping and can pinpoint to specific regions of linkage. Methods for whole genome analysis are described in U.S. Ser. No. 60/327,006, filed Oct. 5, 2001, "Identifying Human SNP Haplotypes, Informative SNPs and Uses Thereof," assigned to the assignee of the present invention and U.S. Ser. No. 10/106,097 "Methods For Genomic Analysis", both incorporated herein by reference for all purposes. Further, the identity of SNPs and SNP haplotype blocks across one representative chromosome, e.g. Chromosome 21, are disclosed in U.S. Ser. No., 60/323,059 filed Sep. 18, 2001, "Human Genomic Polymorphisms" assigned to the assignee of the present invention and U.S. Ser. No. 10/284,444 entitled "Human Genomic Polymorphisms", incorporated herein by reference for all purposes. See also Patil, N. et al, "Blocks of Limited Haplotype Diversity Revealed by High-Resolution Scanning of Human Chromosome 21" *Science* 294, 1719–1723 (2001), disclosing SNPs and haplotype structure of Chromosome 21.

It is desirable to establish new and useful business methods to capitalize on these technological and scientific developments in genetics.

BRIEF SUMMARY

Improved business methods, devices, and systems for utilizing genetic information are provided.

According to one embodiment of the invention, a business method is disclosed that includes the steps of scanning the human genome for single nucleotide polymorphisms across more than 10,000,000 bases including both genic and nongenic regions; grouping the single nucleotide polymorphisms into haplotype blocks; using the haplotype blocks in association studies with a phenotypic state; using associations in a discovery process; and marketing products from the discovery process.

DETAILED DESCRIPTION

As used in the specification, "a" or "an" means one or more. As used in the claim(s), when used in conjunction with the word "comprising", the words "a" or "an" mean one or more. As used herein, "another" means at least a second or more.

Reference now will be made in detail to various embodiments and particular applications of the invention. While the invention will be described in conjunction with the various embodiments and applications, it will be understood that such embodiments and applications are not intended to limit the invention. On the contrary, the invention is intended to cover alternatives, modifications and equivalents that may be included within the spirit and scope of the invention. In addition, throughout this disclosure various patents, patent applications, websites and publications are referenced. Unless otherwise indicated, each is incorporated by reference in its entirety for all purposes. Processes that may be used in specific embodiments of the methods herein are described in more detail in the following patent applications, all of which are specifically incorporated herein by reference: U.S. provisional patent application Ser. No. 60/280,530, filed Mar. 30, 2001; U.S. provisional patent application Ser. No. 60/313,264 filed Aug. 17, 2001; U.S. provisional patent application Ser. No. 60/327,006, filed Oct. 5, 2001, all entitled "Identifying Human SNP Haplotypes, Informative SNPs and Uses Thereof"; U.S. provisional patent application Ser. No. 06/332,550, filed Nov. 26, 2002, entitled "Methods for Genomic Analysis"; U.S. Pat. Ser. No. 10/106,097, filed Mar. 26, 2002, entitled "Methods for Genomic Analysis"; U.S. Ser No. 10/042,819, filed Jan. 7, 2002, entitled "Genetic Analysis Systems and Methods"; and U.S. Ser. No. 10/284,444, filed Sep. 18, 2001, entitled "Human Genomic Polymorphisms", the disclosures all of which are specifically incorporated herein by reference.

All publications mentioned herein are cited for the purpose of describing and disclosing reagents, methodologies and concepts with the present invention. Nothing herein is to be construed as an admission that these references are prior art in relation to the inventions described herein.

I. General.

Scientists have completed the first draft of the genetic sequence of a human being, marking the beginning of a new era in biological research. Although this in itself is a significant accomplishment, much of the business value is in discovering patterns of variation between individuals and correlating specific genomic regions with a phenotypic trait.

Sequencing the human genome has revealed that there is a high degree of homology in genetic information between humans—any two humans share approximately 99.9 percent the same DNA sequence and have the same up to 100,000 or so genes similarly situated in one of twenty-three chromosomes. However, differences still exist. Approximately 0.1 percent, or one out of every 1,000 DNA letters is different between any two humans. This accounts for an estimated of 3 to 4 million common differences (or SNPs) between individuals and many more rare ones.

Most diseases have a genetic basis that is often the result of numerous genetic factors rather than just one gene. Therefore, when scientists want to understand the genetic causes and resulting biological pathways involved in disorders such as Alzheimer's, cancer or asthma, they need to compare the DNA variations of the entire genome of many individuals who have the disease to the genomes of many people who do not have the disease.

Further into the drug commercialization process, drug companies invest hundreds of millions of dollars to develop a new product, only to suffer large losses due to clinical trial participants having unpredictable effects (e.g., increased toxicity or inadequate or no response to the tested drug). In order to overcome negative results, obtain regulatory approval faster and recoup losses, drug companies need to associate effects with genetic profiles of clinical trial participants. It would be very advantageous for drug companies to be able to predict which individuals in a population will tolerate or respond positively to a tested drug, and/or which individuals will experience negative side effects or no significant improvement from the drug.

By scanning an initial set of genomes, the business methods herein identify common SNPs and common "haplotypes" patterns in which "SNPs" occur. Once these haplotypes are known, assays can be used to determine the genetic profiles of many individuals by reading only a few SNPs from each known haplotype block or by reading all SNPs from each known haplotype and using the haplotype blocks to ensure data integrity. The results from these assays can be used, directly or indirectly, in drug discovery, clinical trials and other discovery efforts with partners. The results can save partners millions of dollars in unsuccessful clinical trial and fruitless research and development efforts. Partners can include, for example, biotech partners, pharmaceutical partners, consumer products partners (e.g., in the discovery of shampoos, skin care products and others), agricultural partners, and/or other partners (e.g., scientific partners or government partners).

The tremendous market advantage obtained by pharmaceutical companies (or other companies) as a result of association studies is one of the bases for the business methods and systems herein. In some cases, instead of evaluating all 3 billion bases from each genome, or even the 3 to 4 million common SNPs, it is possible to evaluate as few as 300,000 to 500,000 SNPs or even less in order to make a correlation with the whole genome of an organism. The haplotype patterns detected by reading these particular SNPs provide enough information to allow statistically accurate association data to be extracted from specific populations. Alternatively, if one identifies a large percentage of common SNPs in a genetic region in an association study, the haplotype blocks may be used to verify genotyping results. Pharmaceutical partners, for example, may then pay for the association of human genetic profiles with disease symptoms, drug responses, or other phenotypic states. Agricultural partners, for example, may pay for the association of genetic profiles of various crops with pest resistance, better quality produce, better yields or other phenotypic states. Veterinary partners will pay for association of genetic profiles of various animals with drug resistance, improved performance, increased virility or other phenotypic traits.

Furthermore, one can acquire the rights to drugs that others place at reduced (such as those that failed to gain regulatory approval, failed to meet primary efficacy endpoints in late-stage clinical trials, have serious adverse affects, or are not first-line therapy) and apply this technology herein to determine which patients are best suited for the drug; thereby, significantly increasing the drug's value.

With initial funding from partners and others, the present method provides for a comparison of human DNA with the DNA of various animals and/or other organisms to identify non-genic regions of DNA conserved between species through evolution. These funds may then be used to conduct discovery processes without partners for development of an internal diagnostic and drug pipeline of products.

II. Scientific Basis.

The human body contains about 100 trillion cells. Inside each cell is a center called a nucleus. Inside the nucleus are two sets of twenty-three human chromosomes that contain genetic material. One set of chromosomes is inherited from the mother and the other from the father. Each set includes similar genetic information in similar chromosomal location.

In practice, however, there are subtle differences between paternal and maternal versions of each genome. In fact, except for identical twins, every individual's genome has millions of subtle differences from other individual genomes. These subtle differences account for most of the differences between individuals, for example, eye and skin color. In addition, they can be used to determine an individual's predisposition to diseases, response to drugs, reaction to the environment, and even in some cases, behavior.

The human genome is gigantic. It is often compared to a book written in a four-letter alphabet using a total of three billion letters, or about one billion words. This makes one person's genome as long as 800 Bibles. If one were to read the genome out loud at the rate of one word per second on 8-hour shifts, it would take about a century. It is an immense document, yet it fits inside the microscopic nucleus of a tiny cell that fits easily upon the point of a pin.

Just like a book, the human genome is written in linear, one-dimensional form and is defined by a code that transliterates the four-letter alphabet into a large lexicon of meanings through the order of their groupings. However, whereas English books are written in words of variable lengths using twenty-six letters, genomes are written primarily in three-letter words, using only four letters: adenine, cytosine, guanine and thymine (or in shorthand, A, C, G and T, respectively). Furthermore, instead of being written on flat pages, they are written in long chains or polymers of alternating phosphate and deoxyribose sugar to which the letters or "bases" are attached as side rings. Each human chromosome is composed of a condensed double helix DNA polymer with a complementary DNA polymer strand.

An individual's genomic DNA affects numerous facets of life by providing, for example, the instructions that direct the production of all proteins in the body. Misspellings or "mutations" in DNA produce mistakes in the proteins that are produced by cells, thus affecting the normal function of the cells, or in regulatory elements of the cells. Although the environment often plays a significant role, variations or mutations in DNA are directly related to almost all human diseases, including infectious diseases, cancers, inherited disorders, and autoimmune disorders. Variations in DNA are also responsible for certain "protective" traits, such as a stronger immune system, more rapid clearing of toxins from the organism, or extended lifespan. Being able to compare the DNA of many individuals and associating those variations to clinical symptoms provides a powerful tool for understanding, diagnosis and treatment of a disease or promotion of a health state.

Knowledge of human genetics has led to the realization that many diseases result from either complex interactions of several genes and/or their gene products, from any number of variations within one gene and its resulting gene product, or from any number of variations within the non-coding regulatory regions of genes. For example, Type I and II diabetes have been linked to multiple genes, each with its own pattern of variations.

The complexity of the genetic basis of disease highlights the need for new technology capable of looking across the entire genome to analyze large numbers of variations. Scanning entire genomes, or genomic DNA or derivatives thereof, is one aspect of the business systems and methods disclosed herein.

In one embodiment of the implementation of the systems and methods disclosed herein provides for the separation of the full sets of chromosomes from individuals (such as more than 10, preferably more than 20, more preferably more than 25 and even more preferably more than 50 individual genomes) such that there are multiple unique genomes. Preferably, haploid genomes (or genomes derived from a single set of chromosomes) are used. Techniques for employing haploid genomes are disclosed in U.S. Ser. No. 10/106,097. The bases of all or a significant part of these genomes are then scanned or sequenced using, for example, conventional DNA sequencers or chip-based technologies. In a preferred embodiment, whole-wafer technology from Affymetrix, Inc. of Santa Clara, Calif. is used to read each of the genomes at single-base resolution. DNA sequence data generated from each genome is then compared with the other genomes in order to discover all or many of the variations among the genomes. For example, individual 2 in Table 1 below has two variations as compared with individuals 1 and 3:

TABLE 1

| Individual 1: | T | A | G | T | C | G |
|---|---|---|---|---|---|---|
| Individual 2: | T | A | A | T | C | C |
| Individual 3: | T | A | G | T | C | G |

Because all humans are 99.9% similar in their genetic makeup, most of the letters, or bases, of their genomes will be identical. One would expect to discover up to about 3 to 4 million such common variations between 50 scanned genomes, with "common" variations defined in some cases as those variations that occur in at least 10 percent of people.

Most single nucleotide polymorphisms or "SNPs" do not occur independently but are passed from generation to generation in variable-length blocks of multiple SNPs, forming patterns across the genome that form an individual's genetic profile. These patterns are referred to as "haplotypes." In scanning the first, for example 20 to 50 genomes, it will be possible to identify common haplotypes in which SNPs occur. After identifying these haplotypes it becomes possible to determine the sequence of individuals by reading only a few SNPs from each known block of SNPs. This approach has a tremendous advantage in conducting genetic association studies for pharmaceutical partners, because it utilizes a reduced set of specific SNPs that are indicators for the state of the entire genome. Instead of reading all 3 billion bases from each genome, or even the 3 to 4 million common SNPs that may be found, one may read, for example, only 300,000 to 500,000 informative SNPs, once they are discovered. The haplotype patterns seen by reading these particular SNPs allow statistically accurate association data to be extracted from specific clinical populations. Even when not used to generate association study data, haplotypes are useful for validating association results. For example, after pooled samples are scanned and correlated with a phenotypic trait, individuals can be genotyped for presence or absence of SNPs of haplotypes that are found to be of potential significance in the pooled analysis. The allele SNPs can be used to "check" the genotype of other SNPs of the same haplotype block.

According to one aspect of the invention, glass wafers on which high-density arrays of nucleic acid probes have been placed are used. Each of these wafers holds, for example, approximately 60 million nucleic acid probes that can be used to recognize longer nucleic acid sequences in a sample. The recognition of sample nucleic acids by the set of nucleic acid probes on the glass wafer takes place through the mechanism of hybridization. When a sample nucleic acid hybridizes with an array of nucleic acid probes, the sample will bind to those probes that are complementary to sample nucleic acid sequence. By evaluating the level of hybridization of different probes to the sample nucleic acid, it is possible to determine whether a known sequence of nucleic acid is present or absent in the sample.

The use of probe arrays or wafers to decipher genetic information involves the following steps: design and manufacture of probe arrays or wafers, preparation of the sample, hybridization of target nucleic acids to the array, detection of hybridization events and data analysis to determine sequence. The preferred wafers or probe arrays are manufactured using a process adapted from semiconductor manufacturing to achieve cost effectiveness and high quality, as for example, those manufacture by Affymetrix, Inc.

The design of the wafers or nucleic acid probe arrays begins by probe selection. The probe selection algorithms are based on ability to hybridize to the particular nucleic acid sequence to be scanned. With this information, computer algorithms are used to design photolithographic masks for use in manufacturing the probe arrays.

Probe arrays are preferably manufactured by light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. This parallel process enhances reproducibility and helps achieve economies of scale.

Once fabricated the wafers or nucleic acid probe arrays are ready for hybridization. The nucleic acids to be analyzed (the target) is isolated, amplified and labeled with a fluorescent reporter group. The labeled target is then incubated with the array using a fluidics station and hybridization oven. After the hybridization reaction is complete, the array is inserted into the scanner, where patterns of hybridization are detected. The hybridization data are collected as light emitted from the fluorescent reporter groups already incorporated into the target, which is now bound to the probe array. Probes that most clearly match the target produce stronger signals than those that have mismatches. Since the sequence and position of each probe on the array are known, by complementarity, the identity of the target nucleic acid applied to the probe array can be identified.

The data and information generated by the scientific assays disclosed is valuable to numerous industries. For example, information concerning potential drug targets is highly valuable to the biotech industry and can greatly speed up the drug discovery process, and hence time-to-market. Similarly, information concerning the effectiveness and efficiency of given drug is extremely valuable to the pharmaceutical industry and can save a company substantial money in lost revenue due to failures in clinical trials. The information generated herein may also be valuable to the agricultural industry, veterinary medicine industry, consumer products industry, insurance and healthcare provider industry and forest management (by providing genetic basis for useful traits in plants, trees, laboratory animals and domestic animals) for example.

III. Business Applications

The drug research and development process includes everything from the discovery of target genomic regions to drug discovery and final product launch. This process is currently very lengthy, expensive and risky. On average, it takes fourteen years to develop a product from the initial research laboratory period to FDA approval. Any event that delays the commercialization or development process of a potential drug can cost the affected company a loss of revenue of up to $1 billion annually. Conversely, any change that can accelerate commercialization or development cycle of a potential drug can bring significant financial benefits to the affected company that implements such changes.

Accelerated time-to-market not only brings the benefit of earlier sales revenues but the expanded market share enjoyed by companies that are the first to enter a segment before its competitors. This is critical, because the period of market exclusivity for the first drug in a new market therapeutic class is typically much shorter than would be desirable. Consequently, marketing expenditures have increased rapidly as companies attempt to maintain or increase market share.

In addition to the time-to-market factors, the odds of any compound successfully making it through all of the steps across fourteen years are miniscule. Statistically, out of 5,000 compounds that begin in pre-clinical development, only five make it to clinical trials, and only one is likely to reach the market. The combination of long development cycles and high failure rates results in an average cost of approximately $500 million for making a successful FDA approved compound. Therefore, business systems and methods that improve the efficiency and timeliness of regulatory approval are greatly valuable.

Pharmaceutical companies have recognized the need to improve research and development efficiency by utilizing genomics in their drug discovery programs. This effort is necessary for companies to match historical revenue growth levels and to meet shareholders' expectations. The drive by pharmaceutical companies for efficiency provides an opportunity for application of genome-wide scanning technologies during both the research and clinical development cycle.

One example of the application of the business systems and methods herein can be found in population segmentation. It is generally acknowledged that most drugs work more effectively for some patients than others. Because this variability in patient response is often poorly understood, pharmaceutical companies may unnecessarily discontinue further drug development, fail to obtain regulatory approvals for promising drug candidates, or if approvals are obtained, be unable to market an approved drug effectively or to obtain approval for third party reimbursement.

Genomic differences have long been recognized as influencing how patients respond to drugs. However, pharmaceutical companies generally have not considered genomic differences between patients in developing and implementing clinical trials or in the marketing of approved drugs. By correlating genomic variation with drug response in clinical trials, it is possible to improve the drug development and marketing process. For example, pharmaceutical companies could use the correlation data from earlier stages of clinical trials to make more informed decisions on whether or not to continue trials, enter later-phases of trials or which patients to enroll in later-stages (e.g., phase III or IV). For example, enrolling patients with genetic predisposition for positive drug response can improve the therapeutic index for these patients and improve the possibility of regulatory approval. Furthermore, understanding the correlation between genomic differences and drug response can enable pharmaceutical companies to improve drug marketing by identifying segments of the population for whom particular drugs are likely to be more effective than other drugs, and encouraging physicians to preferentially prescribe such drugs to these patients. Marketing to physicians can be accomplished by continuing medical education, peer-review journals, Internet, print advertising or direct sale calls. In addition, by using the information disclosed herein a company can better market a drug by segregating a responder population from a non-responder population, or by segregating a population that encounters negative side effects (or even toxicity) from a population that does not suffer negative effects. This may further allow a company to keep a drug on the market that would otherwise be withdrawn or to reintroduce a drug that has already been withdrawn due to adverse effects. The information generated can also be used to create diagnostic kits.

Drugs are typically developed to interact with a single version of a gene product, e.g., protein or receptor in the human body. A drug may therefore, for example, only be effective in individuals that have a particular variation encoding the specific protein or receptor for which the drug was designed. Individuals, who do not have a genetically caused variation in these regions or in regions involved in the metabolism of the drug, may not respond to the drug or may experience adverse side effects, such as increased toxicity for example.

The methods used by the pharmaceutical industry to develop new drugs and to improve existing drugs may be changed when genetic variations are taken into account. Genetic variations may play a significant role in all stages of research and development and drug discovery. Genetic variation information can also be used to improve drugs already on the market by providing information to better select drugs for a particular patient.

To further illustrate the difficulties solved herein, drugs can interact, directly and/or indirectly, with a variety of different proteins that are encoded and regulated by different genomic regions. Therefore, more than one genomic region can determine how an individual responds to a given drug. The inventions herein can be used to identify such multiple regions. As genetic variations are better understood, it is clear that an individual's response to a given drug is dependent upon that individual's unique genome or more specifically variations within the genome.

A practical approach to understanding why different individuals respond differently to the same drug is found in grouping individuals together based upon specific genomic similarities or similar haplotype patterns. These genomic similarities can occur between unrelated individuals from different ethnic groups and/or from different geographic regions. The ability to identify and associate genetic variations with a phenotypic state (e.g., disease and drug responses) across the entire genome can facilitate the entire drug development process and can reduce the time-to-market for therapeutics. For example, genetic profiles of select subsets of patient populations may be used to enable pharmaceutical companies to identify drug targets, focus on potentially better leads and move quicker into screening assays. In addition, better drug targets can also provide for safer, more effective points of therapeutic intervention.

Markets that may be addressed by the business systems and methods disclosed herein include, but are not limited to, evaluation of genetic variations and drug response, evaluation of genetic variations to identify and validate target regions, evaluation of variation and susceptibility to disease, identification of conserved non-coding regions that may contain gene regulatory sequences, evaluation of genetic variations and regulatory regions affecting development, and evaluation of other genotype-phenotype associations with commercial potential, such as in consumer products and agriculture. Potential customers or partners for genome-wide pattern information, conserved region information, patient profiling services and other scientific partnerships include, for example, numerous companies in the pharmaceutical, biotechnology and agricultural industries, as well as academic centers and government research institutes.

Other potential customers or partners for association studies include, for example, healthcare providers, insurance companies, government entities (e.g., Medicaid, Medicare) and employers or any other entity interested in achieving more economical or effective system for providing or paying for medical or life insurance. Such parties can utilize association studies, for example, to selectively approve expensive drugs to patients who are correlated with a susceptibility to an adverse reaction from a generic drug, evaluate better an individual's likelihood to suffer from disease (or die) prior to underwriting them and selecting more effectively health and life insurance premiums for individuals. These parties may provide funding and/or sample sources for the association studies herein.

The business systems and methods herein further include, for example, the development of DNA-scanning and wafer technology and use of that technology's genome scanning capabilities for identifying commercially valuable genetic regions through research collaboration, and verifying such results using associations studies. Up-front fees, research payments, milestone payments, database subscriptions, product sales and royalties may all contribute revenue to the business model.

In the short-term, the business strategies and methods herein can generate revenues through several means. First, revenue can be generated by providing genomic data obtained and analyzed from large scale scanning of genomes. Such data can further be used, for example, for genotyping and association studies and can further be licensed to biotechnology, pharmaceutical, or other interested parties on a non-exclusive basis. In addition or alternatively, revenue can be generated by entering into discovery contracts on an exclusive or non-exclusive basis with biotech, pharmaceutical, or other companies that are interested in specific areas of the genome, or specific disease areas across portions or all of the genome, even before scanning the first genomes. Any of the methods herein may be used to verify (or remove) existing drug target candidates. Furthermore, the business methods herein can be used to identify SNPs and haplotypes thereof of regions conserved with other species. This can be used for cross species studies.

In the mid-term, the business strategies herein encompass generating revenue through at least five means. This can add or replace other sources of revenue. First, collaboration agreements can be entered into to provide genome-wide sequencing and genetic profiling (association studies) services that enable biotechnology, pharmaceutical and/or other partners to analyze specific populations. The populations may comprise, for example, of individuals affected by a particular disease, participants in clinical trials or groups displaying a particular response to a drug or environmental stimulus. Portions of the intellectual property from such efforts may be retained by the company performing such studies. The company performing the studies may then further develop drug targets and/or diagnostic products based on the retained intellectual property. Second, contract and/or grant funding from non-profit grant-giving organizations such as the federal government may be used for either haplotype discovery or association studies. Third, drugs can be in-licensed where genome-wide association studies are expected to add significant value, and then out-licensed at a premium to other companies or in exchange for substantial milestones and royalties after identification of the genetic basis of, for example, a drug metabolism response. Fourth, pharmaceutical partners can contract for research funded by those pharmaceutical partners. Furthermore, as part of an inter-company cross-licensing agreement, chip or other platform suppliers will pay a royalty on sales to its customers of chips or other technologies containing content generated by the business.

In the longer term, royalties from products (e.g., drugs and diagnostics) developed and commercialized can generate revenue. Such products include, for example, products previously in-licensed, products developed and/or commercialized independently using internal pharmaceutical development efforts and products developed in collaboration with partner(s). The association studies linking particular genetic variations and clinical symptoms will be extremely valuable in identifying drug targets as well as optimizing existing therapies. Agreements with pharmaceutical and biotechnology companies entered will include royalty rights on products derived from this data.

Importantly, generated revenue can be used to conduct similar or different internal pharmaceutical development efforts that can potentially lead to the development of commercial products.

IV. Business Flow

Figure 1:
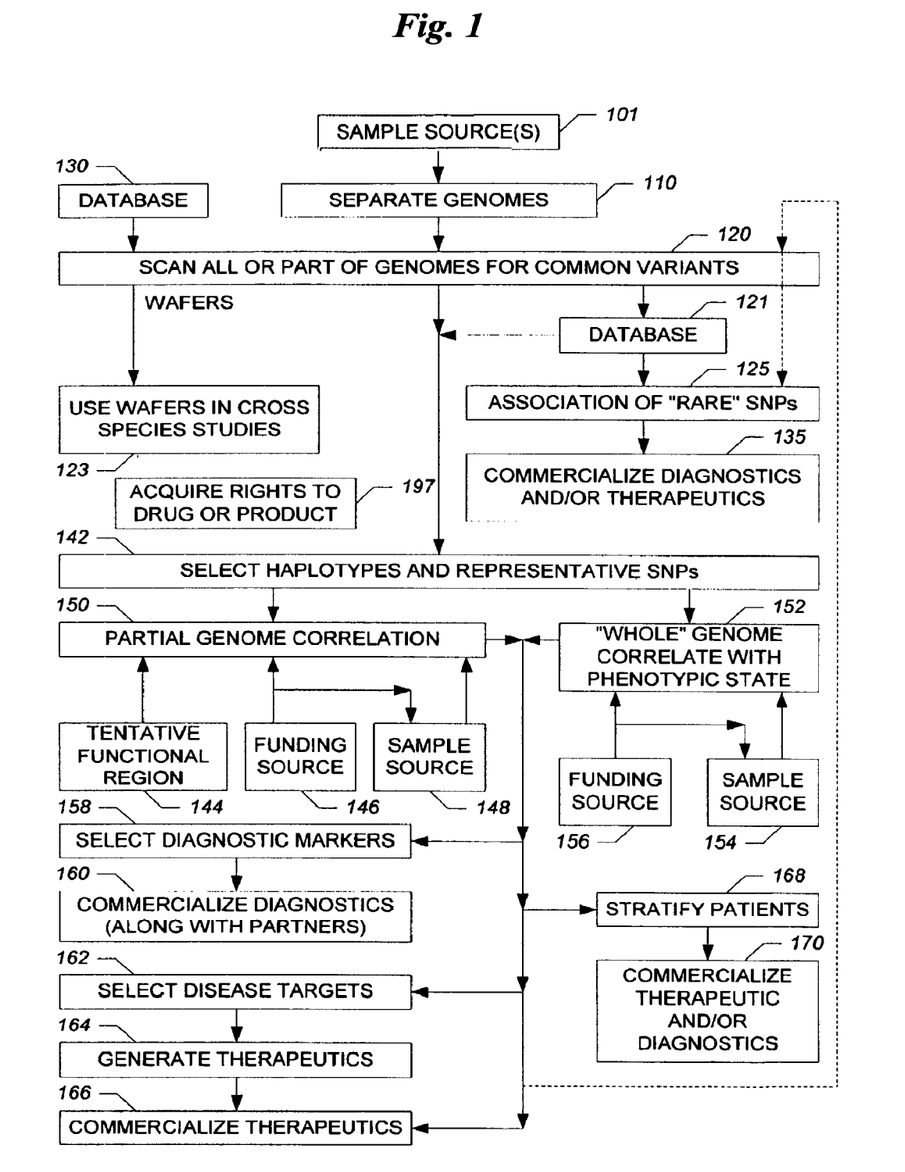
FIG. 1 is a flow chart illustrating aspects of the business method herein.

FIG. 1 illustrates overall steps in the business systems and methods herein. As shown, at step 101 initial genomic samples are obtained. Samples of clinical population can be obtained from, for example, hospitals or universities. Other partners or entities can also provide sample sources. In most embodiments, the sample sources will include genomic DNA or derivatives thereof from human sources although other organisms can be utilized as well. At this stage the samples need not be from sample or control groups. The samples are preferably collected from a diverse group, such as from different ethnic background or different geographic regions. Examples of different ethnic backgrounds include Asian, Middle-Eastern, African, Nordic, South Pacific, etc. Further sub-groups may also be compared.

At step 110 the chromosomes are preferably separated to form individual chromosomes. Such separation utilizes, in a preferred embodiment, somatic cell hybrid technology as described in U.S. Ser. No. 10/106,097, claiming priority to U.S. Ser. No. 60/332,550, filed Nov. 26, 2001, entitled "Methods of Genomic Analysis," incorporated herein by reference for all purposes.

At step 120 the genomes are scanned for variants from a baseline sequence in a reference database 130. Variants can include, for example, SNPs or contiguous stretches of genomic DNA (variant DNA stretches) comprising one or more SNPs. Stretches of genomic DNA can comprise of at least 1000 contiguous bases, at least 5,000 contiguous bases, at least 10,000 contiguous bases, at least 50,000 contiguous bases, at least 100,000 contiguous bases or at least 500,000 contiguous bases. Furthermore, variant DNA stretches can comprise of at least 1 SNP, at least 5 SNPs, at least 10 SNPs, at least 25 SNPs, at least 50 SNPs, or at least 100 SNPs. The reference database may be proprietary or a public database such as GenBank. Preferably, more than 10 different sources are scanned (it being understood that a single organism contains the genetic code from two different sources). In more preferred embodiments, more than 20 different sources are scanned, preferably more than 25 different sources, more preferably more than 30 different sources, preferably more than 50 different sources, and more preferably more than 100 sources are scanned. As described in U.S. Ser. No. 10/042,819, entitled "Genetic Analysis Systems and Methods," filed on Jan. 7, 2002, assigned to assignee, the scanning step may be a one-step or two-step process. In a two-step process each consecutive base in a genetic sequence is analyzed initially, and only those variants that are identified in the initial step are utilized for scanning in later grouping processes. The scanning step can utilize a number of technology platforms such as chips, capillary or gel based DNA sequencers, microtiter hybridization wells or others. The genomes that are scanned are preferably from genetically diverse groups such as, for example, different racial groups, ethnic groups or geographic locations. This is based on the assumption that evolutionarily older SNPs that have more global applicability are common SNPs. However, specific groups or sub-groups can also be scanned to identify variants that are more useful for those sub-populations.

Preferably, the entire genetic code in the reference database 130 is analyzed or scanned for variants. Preferably, at least the non-repeat regions of the reference database are analyzed to identify SNPs and preferably common SNPs. Preferably, gene and non-gene regions of the sequences in the database are analyzed. Preferably, more than 1,000,000 bases are analyzed, preferably more than 10,000,000, more preferably more than 100,000,000, more preferably more than 500,000,000, and more preferably more than 1,000,000,000 bases. Preferably, more than 50% of at least one chromosome is scanned in multiple samples, preferably more than two chromosomes, preferably more than five chromosomes, and most preferably all of the chromosomes in the particular organism under study. By "common" SNPs, it is intended to refer to SNPs occurring in more than 2% of the sample population studied, preferably more than 4% of the population studied, preferably more than 6% of the population studied, preferably more than 8% of the population studied, and more preferably more than 10% of the population studied. Of course, rare SNPs can also be utilized in particular association studies at step 125 for commercialization of diagnostics and therapeutics and at step 135 as an adjunct to the other methods herein. "Rare" SNPs are non-common SNPs. Furthermore, the wafers or arrays used herein may also be used to compare genomes of, e.g. humans with other organisms such as mouse, rat or dog to, e.g. identify conserved regions as step 123.

The SNPs, haplotype blocks and other variant information such as variant DNA stretches can be stored in a database 121, which may be, in whole or in part, licensed directly for revenue. In addition, in one embodiment, the common variants identified at step 120 are placed in haplotype blocks. This can be accomplished, for example, using the methods disclosed in U.S. Ser. No. 60/280,530, filed Mar. 30, 2001; U.S. Ser. No. 60/313,264, filed Aug. 17, 2001; U.S. Ser. No. 60/327,006, filed Oct. 5, 2001; U.S. Ser. No. 60/332,550, filed Nov. 26, 2001; and U.S. Ser. No. 10/106,097, filed Mar. 26, 2002, previously incorporated herein by reference. Representative variants and haplotype blocks from an entire human chromosome (chromosome 21) are disclosed in, for example, in Patil, N. et al, "Blocks of Limited Haplotype Diversity Revealed by High-Resolution Scanning of Human Chromosome 21" *Science* 294, 1719–1723 (2001) and the associated supplemental materials, incorporated herein by reference. At step 142, representative SNPs or variant DNA stretches are selected from among the haplotype blocks to be used in association studies.

The SNPs or variant DNA stretches selected at step 142 may be used in a variety of applications. For example, in collaboration with other companies, one may select portions of the genome of an organism at step 144 that are believed to play a role in a particular phenotype such as a disease state. A partner may or may not provide the funding at step 146 and/or a sample set, for example, of disease and control samples, at step 148.

At step 150 SNP's, representative SNPs or variant DNA stretches from each sample are used in one or more assays to determine which portions of the tentatively selected functional region correlate in fact with the phenotype of interest. Such assays include, for example, a chip based assay, Invader assay, Taqman assay, GeneEngine sequencer, Pyrosequencing assay, MassArray assay, BeadArray assay, or gel or capillary sequencing assay (various of the above being trademarks). An Invader assay is based on enzyme-substrate reaction for quantifying DNA and RNA by binding two short DNA probes to a target, enzymatically cleaving the target, binding a fluorescently labeled probe to the cleavage site and then cutting the probe bout DNA to detect a fluorescence signal. A Taqman assay is a fluorogenic probe-based assay available from Applied Biosystems (Foster City, Calif.). A GeneEngine assay feeds DNA through small channels and then scans the DNA using high-speed optics. A Pyrosequencing assay is a sequencing-by-synthesis assay available from Biotage AB (Westborough, Mass.). A MassArray assay assembles sequence information using mass spectrometry by obtaining base-specific chain termination information using enzymatic reactions. The BeadArry utilizes light conducting fiber optic bundle substrates that are composed of 3-micron beads. Gel and capillary sequencing operations as well as other assays are well known to those skilled in the art.

The funding for use in the business methods herein will normally take on multiple forms. For example, the funding may be by way of funding for costs of performing the particular study in question, in some cases with margin. In addition funding may be provided by way of milestone payments, for example, at the time the SNPs/haplotypes are identified in a region, at the time the association study is completed, at the time research results are confirmed, at the time clinical trials of various stages are started and/or completed, at the time drugs or diagnostics begin to be marketed and/or reach sales milestones, and/or royalties on sales of the relevant drug, diagnostic, or drug sold in conjunction with the population segregation diagnostic, or similar fees for other products such as agricultural products or consumer products. In addition, particular partners may provide funding by way of equity investment, and/or equity may be sold to investors.

Alternatively, or in addition, at step 152 whole genome studies are performed whereby the SNPs or variant DNA stretches from all or substantial part of the genome, are correlated with a phenotypic state such as a disease state, for example. This correlation may also be conducted through pooling samples to reduce overall costs or by genotyping individual samples. This step may also be performed in collaboration with others, who may provide samples at step 154 and/or funding at step 156. Of course, the sample source and the funding source may or may not be the same in each of the studies herein. In one example, the funding source may be a pharmaceutical company and the source of samples may be a hospital, academic research center or other company. In another example, the funding source and/or sample source may be from an insurance company, government entity or employer.

In one embodiment, at step 197 rights to a drug or product are acquired prior to initiating association studies. Such drug or product may be, for example, one that has been pulled off the market due to unpredictable adverse effects in a small group of individuals or may be one that did not obtain regulatory approval due to a large number of individuals experiencing unanticipated effects in clinical trials. The company may then be able to use association studies to correlate between genomic differences and drug responses and create a diagnostic kit to identify patients who may benefit from the drug. Thus, by stratifying patients and identifying outlier individuals, a company may be able to both obtain regulatory approval and increase drastically the value of its acquired drugs.

A number of activities can be based upon the results of steps 150 and 152. For example, at step 158 diagnostic markers may be used to develop diagnostic tests that are indicative of a patient's tendency to a disease (or, for example, being a carrier of a disease variant). Based on the markers, the diagnostics may be developed and commercialized at step 160. The diagnostics may take on a number of forms such as immunoassays, chip based DNA assays, PCR assays, Taqman™ assays, sequencing based assays or the like.

In addition, or in the alternative, at step 162 the correlation studies are used to select disease targets for drug development. Once a genetic locus or multiple loci in the genome are associated with a particular phenotypic trait, for example, a disease susceptibility locus, the gene(s) or regulatory element(s) responsible for the trait can be identified. These gene(s) or regulatory element(s) may then be used as therapeutic targets for the treatment of the disease, as shown at step 164, or for commercialization, as shown at step 166, independently or in collaboration with partners.

In addition, or in the alternative, at step 168 the phenotypic trait of drug response is used to stratify patients into various groups. The groups may be, for example, those that respond to a drug versus those that do not respond, those that respond to a drug without toxic effects, versus those that are observed to have toxic effects. At step 170 the therapeutic may be marketed with an associated diagnostic that is capable of segregating those that will respond an acceptable manner to the drug from those that do not.

Figure 2:
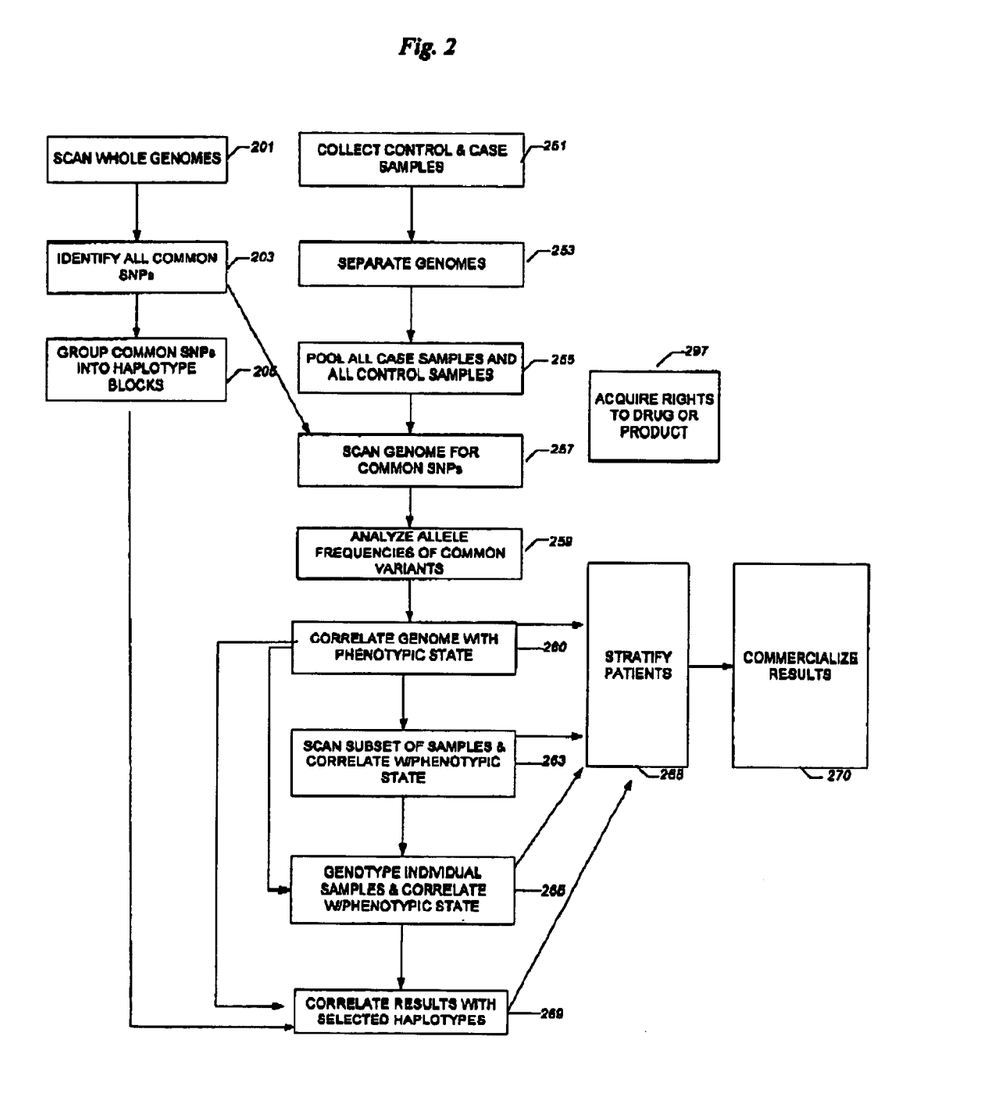
FIG. 2 is a flow chart illustrating an automotive aspect of the business method herein.

FIG. 2 illustrates another embodiment of the methods and systems herein. At step 201, a plurality of whole genomes is scanned to identify all variants. Table II, row 1 below, illustrates a contiguous stretch of genomic DNA with all identified variants. At this stage, the variants may include common SNPs, rare SNPs and variant DNA stretches. Each SNP is illustrated by a framed base. A first and second alleles are further illustrated.

Next at step 203, common variants and variant DNA stretches are identified, and at step 205 common variants are grouped into haplotype blocks using any one or more of the methods herein. Table II, row 2, illustrates common SNPs grouped into two haplotype blocks. Starting from the left of the genomic sequence, variants C, T, A in allele 1 and the respective allele variants T, C and G in allele 2 form a first haplotype block whose bases are illustrated in bold; next, variants C, C, A and their respective allele variants A, T, and G form a second haplotype block whose bases are illustrated in underline; furthermore, common variants T an C in allele 1 and G in allele 2 form a third haplotype block illustrated in bold and italic. These common SNPs and haplotype blocks can be used in pooled association studies as described below.

After case and control samples sources are obtained at step 251 and their genomes are separated at step 253 (using any of the methods disclosed herein), all control genomes and all case genomes are "pooled" together at step 255. The pooled genomes are scanned at step 257 to identify all common variants or variant DNA stretches identified at step 205 using any of the methods herein. Table II, row 3, illustrates an example of results from scanning pooled case and control genomes.

After scanning both pooled cases and controls for common variants or variant DNA stretches, the relative allele frequencies of common variants are analyzed at step 259. If the frequencies of two allele variants are substantially the same, such as, when each allele appears in approximately 50% of all samples, the allele variants cannot be used for correlation purposes and are excluded from further analyses. On the other hand, if the frequencies of two allele variants are not substantially similar, a common variant is identified which can be used to correlate a particular genotype with a phenotypic state of interest. Table II, row 4, illustrates three different relative allele frequencies. The variants on the left end of the genomic sequence (C, T, A, C, C and A in allele 1 and T, C, G, A, T and G in allele 2) are expressed at either very high or low frequencies (e.g., 1%, 2%, 98% or 99%) and therefore are variants (or encompassed within variant DNA stretches) that can be used for correlation. On the other hand, the variants on the right end of the genomic sequence (T and C in allele 1; and G and G in allele 2) are expressed in roughly half the genomes (e.g., 55% and 45%) and cannot be used for correlation; therefore, these variants are excluded from further analysis in the example in Table II.

The common variants and variant DNA stretches (C, T, A, C, C and A in allele 1 and T, C, G, A, T and G in allele 2) are then used in association studies to correlate genomic regions with a phenotypic state of interest at step 260. This is often referred to as a first round of association. Most often, only some of the common variants will be found to correlate with a phenotypic state. However, at this stage, even variants that show a relatively low degree of correlation are retained for further analysis. Table II, row 5, illustrates an example wherein only three of the six remaining variants are correlated to a phenotypic state of interest. Common variants or variant DNA stretches that are not correlated to a phenotypic state are excluded from further analysis.

The variants (including variant DNA stretches) correlated in the first round of association can then be verified by scanning a subset of pooled samples for the highly correlated regions identified in the first round of association at step 263 (T, C, G in allele 1 and C, T, and A in allele 2). If a subset of pooled samples shows identical results after a second round of association, the samples are retained for further analysis. In a more preferred embodiment, the correlated variants (or variant DNA stretches) are verified by genotyping individual samples at step 265. Genotyping may also be considered a second round of association. Table II, row 6, illustrates an example of verifying highly correlated variants or variant DNA stretches by genotyping individual case and control samples. In this example, samples 1 and 2 are case samples, while samples 3 and 4 are control samples. In sample 1, all variants are identical to those in the pooled genomes; therefore, sample 1 corroborates variants T, C, and G (or a genomic stretch encompassing those variants) are correlated with a phenotypic state and the sample is retained for further studies. Conversely, the variants in sample 2 (C, T and A) are not identical to those in the pooled case genomes; therefore, sample 2 can be either genotyped again (to verify results) or excluded from further analysis. By analogy, sample 3 corroborates that variants C, T, and A are correlated with a control phenotypic state, and therefore this sample is retained for further investigation. On the other hand, sample 4 does not have all of the requisite variants to correlate to a control phenotypic state and is excluded from further studies.

In addition to genotyping individual samples, the haplotype blocks identified at step 205 can also be used to verify highly correlated variants or variant DNA stretches from the first round of association. In particular, after genotyping a sample for highly correlated variants, haplotype blocks can be used to verify genotyping results, as further illustrated in Table II, row 7. In this example, haplotype block 1 is C-T-A and haplotype block 2 is T-C-G. Samples 1 and 3 align with the haplotype blocks 1 and 2, respectively. Aligning with a haplotype block can confirm variants from first and/or second rounds of association. On the contrary, samples 2 and 4 do not perfectly aligned with a haplotype block and therefore cannot corroborate the pooled correlation study. Therefore, these samples are excluded from further analysis.

TABLE II

1    Scan whole genomes to identify variants:

[C]G A[T]C T G[A]G C G[C]C C[C]T T[A]A C[T][T][C] (allele 1)  (SEQ ID NO: 1)

[T]G A[C]C T G[G]G C G[A]C C[T]T T[G]A C[G][T][G] (allele 2)  (SEQ ID NO: 2)

2    Identify common variants and group into haplotype blocks:

[C]G A[T]C T G[A]G C G[C]C C[C]T T[A]A C[*T*][T][C] (allele 1)  (SEQ ID NO: 3)

[T]G A[C]C T G[G]G C G[A]C C[T]T T[G]A C[*G*][T][G] (allele 2)  (SEQ ID NO: 4)

TABLE II-continued

3   Scan "pooled" control and case genomes for all variants

Case:    T G A C T G G C G C C C T T A A C T T C   (SEQ ID NO: 5)

Control: C G A T C T G A G C G A C C T T G A C G T G   (SEQ ID NO: 6)

4   Identify More Common Variants By Relative Allele Frequency

C$^{2\%}$ G A T$^{2\%}$ C T G A$^{2\%}$ G C G C$^{99\%}$ C C C$^{99\%}$ T T A$^{99\%}$ A C T$^{55\%}$ T C$^{55\%}$ (allele 1)

(SEQ ID NO: 7)

T$^{98\%}$ G A C$^{98\%}$ C T G G$^{98\%}$ G C G A$^{1\%}$ C C T$^{1\%}$ T T G$^{1\%}$ A C G$^{45\%}$ T G$^{45\%}$ (allele 2)

(SEQ ID NO: 8)

5   Common variants:

Case:    T G A C T G G C G C C C T T A A C G T C   (SEQ ID NO: 9)

Control: C G A T C T G A G C G A C C T T G A C G T G   (SEQ ID NO: 10)

Correlate common variants with phenotypic state

Case:    T G A C T G G C G C C C C T T A A C G T C   (SEQ ID NO: 11)

Control: C G A T C T G A G C G A C C T T T G A C G T G   (SEQ ID NO: 12)

6   Highly correlated variants are verified by genotyping
    Case Samples:

Sample 1: T G A C C T G G G C G C C C C T T G A C G T C   (SEQ ID NO: 13)

Sample 2: T G A C C T G T G C G C C C C T T G A C G T G   (SEQ ID NO: 14)

Control Samples:

Sample 3: C G A T C T G A G C G A C C T T T G A C G T C   (SEQ ID NO: 15)

Sample 4: C G A G C T G A G C G A C C T T T G A C G T G   (SEQ ID NO: 16)

7   Corroborate Using Selected Haplotype Block

Haplotype 1: C G A T C T G A              (SEQ ID NO: 17)

Haplotype 2: T G A C C T G G              (SEQ ID NO: 18)

Case Samples:

Sample 1: T G A C C T G G G C G C C C C T T G A C G T C   (SEQ ID NO: 19)

Sample 2: T G A C C T G T G C G C C C C T T G A C G T G   (SEQ ID NO: 20)

Control Samples:

Sample 3: C G A T C T G A G C G A C C T T T G A C G T C   (SEQ ID NO: 21)

Sample 4: C G A G C T G A G C G A C C T T T G A C G T G   (SEQ ID NO: 22)

The results obtained from steps 260, 263, 265, and 269 can be used for one or more of the applications previously described herein, for example, the development of diagnostic markers, kits and reagents for identifying a phenotypic trait of interest, or the identification of target genomic regions for drug discovery. Any of these applications can be accomplished independently or in collaboration with partners.

The genomic sequences identified by the methods of the present invention may be genic or nongenic sequences. The term identified "gene" is intended to mean the open reading frame encoding specific polypeptides, intronic regions, generally as well as adjacent 5' and 3' non-coding nucleotide sequences involved in the regulation of expression of the gene up to about 10 kb beyond the coding region, but possibly further in either direction. The coding sequences (ORFs) of an identified gene may affect a phenotype state by affecting protein structure. Alternatively, the non-coding sequences of the identified gene or nongenic sequences may affect a phenotype state by impacting the level of expression or specificity of expression of a protein.

Genomic sequences are studied generally by isolating the identified genomic sequence such that it is substantially free of other nucleic acid sequences that do not include the sequence of interest. The sequences are used in a variety of ways. For example, the nucleic acid sequence may be used to detect or quantify expression of a gene in a biological specimen. The manner in which one probes cells for the presence of particular nucleotide sequences is well established in the literature and does not require elaboration here, see, e.g., Sambrook, et al., *Molecular Cloning: A Laboratory Manual* (Cold Spring Harbor Laboratory, New York) (1989).

Alternatively, individuals may be studied that are resistant to a particular disease, such as HIV. By understanding the genetic basis of disease resistance it may be possible to identify therapeutic and/or diagnostic targets. In addition, individuals may be selected for desirable traits such as, for example, healthy state, enhanced performance state, protective state, extended longevity and resistance state.

According to one aspect of the business systems and methods disclosed herein, when a region of the genome has been identified as playing a role in a phenotypic state, after a first, second or any subsequent rounds of association studies, the genome may be the subject of further SNP scanning at steps 120, 260, 263 or 265, for example to identify rare SNPs that may be associated with a disease. These SNPs may play a role in, for example, rare forms of the disease.

In addition, the sequence of the gene (including flanking promoter regions and coding regions) may be mutated in various ways known in the art to generate targeted changes in promoter strength, or changes in the sequence of the encoded protein, etc. The sequence changes may be substitutions, translocations, insertions or deletions. Deletions may further include larger changes, such as deletions of a domain or exon. Techniques for in vitro mutagenesis of cloned genes are known. Examples of protocols for site-specific mutagenesis may be found in Gustin, et al., *Biotechniques* 14:22 (1993); Barany, *Gene* 37:111–23 (1985); Colicelli, et al., *Mol. Gen. Genet.* 199:537–9 (1985); Prentki, et al., *Gene* 29:303–13 (1984); Sambrook, et al., *Molecular Cloning: A Laboratory Manual* (Cold Spring Harbor Press) pp. 15.3–15.108 (1989); Weiner, et al., *Gene* 126:35–41 (1993); Sayers, et al., *Biotechniques* 13:592–6 (1992); Jones and Winistorfer, *Biotechniques* 12:528–30 (1992); and Barton, et al., *Nucleic Acids Res.* 18:7349–55 (1990). Such mutated genes may be used to study structure/function relationships of the protein product, or to alter the properties of the protein that affect its function or regulation.

The identified gene may be employed for producing all or portions of the resulting polypeptide, or protein. To express a protein product, an expression cassette incorporating the identified gene may be employed. The expression cassette or vector generally provides a transcriptional and translational initiation region, which may be inducible or constitutive, where the coding region is operably linked under the transcriptional control of the transcriptional initiation region, and a transcriptional and translational termination region. These control regions may be native to the identified gene, or may be derived from exogenous sources.

The polypeptide may be expressed in prokaryotes or eukaryotes in accordance with conventional methods, depending upon the purpose for expression. For large-scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In many situations, it may be desirable to express the gene in eukaryotic cells, where the gene will benefit from native folding and post-translational modifications. Small peptides also can be synthesized in the laboratory. With the availability of the protein or fragments thereof in large amounts, the protein may be isolated and purified in accordance with conventional ways. A lysate may be prepared of the expression host and the protein purified using HPLC, exclusion chromatography, gel electrophoresis, affinity chromatography, or other purification technique.

An expressed protein may be used for the production of antibodies, where short fragments induce the expression of antibodies specific for the particular polypeptide, and larger fragments or the entire protein allow for the production of antibodies over the surface of the polypeptide (polyclonal antibodies). Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes are immortalized by cell fusion and screened for high affinity antibody binding. The immortalized cells, e.g., hybridomas, producing the desired antibodies may then be expanded. For further description, see *Monoclonal Antibodies: A Laboratory Manual*, Harlow and Lane, eds. (Cold Spring Harbor Laboratories, Cold Spring Harbor, N.Y.) (1988). If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

The identified genes, gene fragments, or the encoded protein or protein fragments may be useful in gene therapy to treat degenerative and other disorders. For example, expression vectors may be used to introduce the identified gene (or variant thereof) into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to be transiently or stably maintained in the cells. The gene or protein product may be introduced into tissues or host cells by any number of routes, including viral infection, microinjection, or fusion of vesicles. Jet injection may also be used for intramuscular administration, as described by Furth, et al., *Anal. Biochem*, 205:365–68 (1992). Alternatively, the DNA may be coated onto gold microparticles, and delivered intradermally by a particle bombardment device, or "gene gun" as described in the literature (see, for example, Tang, et al., *Nature*, 356:152–54 (1992)).

Antisense molecules can be used to down-regulate expression of the identified gene in cells. The antisense reagent may be antisense oligonucleotides, particularly synthetic antisense oligonucleotides having chemical modifications, or nucleic acid constructs that express such antisense molecules as RNA. The antisense sequence may be complementary to the mRNA of the targeted gene, and inhibits expression of the targeted gene products. Antisense molecules inhibit gene expression through various mechanisms, e.g., by reducing the amount of mRNA available for translation, through activation of RNAse H, or by steric hindrance. One or a combination of antisense molecules may be administered, where a combination may comprise multiple different sequences.

As an alternative to antisense inhibitors, catalytic nucleic acid compounds, e.g., ribozymes, anti-sense conjugates, etc., may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman, et al., *Nucl. Acids Res.* 23:4434–42 (1995)). Examples of oligonucleotides with catalytic activity are described in WO 9506764. Conjugates of antisense oligonucleotides with a metal complex, e.g. terpyridylCu(II), capable of mediating mRNA hydrolysis are described in Bashkin, et al., *Appl. Biochem. Biotechnol.* 54:43–56 (1995).

In addition to using the identified sequences for gene therapy, the identified nucleic acids can be used to generate genetically modified non-human animals to create animal models of diseases or to generate site-specific gene modifications in cell lines for the study of protein function or regulation. The term "transgenic" is intended to encompass genetically modified animals having an exogenous gene that is stably transmitted in the host cells where the gene may be altered in sequence to produce a modified protein, or having an exogenous promoter operably linked to a reporter gene. Transgenic animals may be made through homologous recombination, where the gene locus is altered. Alternatively, a nucleic acid construct is randomly integrated into the genome. Vectors for stable integration include plasmids, retroviruses and other animal viruses, YACs, and the like. Of interest are transgenic mammals, e.g., cows, pigs, goats, horses, etc., and, particularly, rodents, e.g., rats, mice, etc.

Investigation of genetic function may also utilize non-mammalian models, particularly using those organisms that are biologically and genetically well-characterized, such as *C. elegans, D. melanogaster* and *S. cerevisiae*. The subject gene sequences may be used to knock-out corresponding gene function or to complement defined genetic lesions in order to determine the physiological and biochemical pathways involved in protein function. Drug screening may be performed in combination with complementation or knock-out studies, e.g., to study progression of degenerative disease, to test therapies, or for drug discovery.

In addition, the modified cells or animals are useful in the study of protein function and regulation. For example, a series of small deletions and/or substitutions may be made in the identified gene to determine the role of different domains in enzymatic activity, cell transport or localization, etc. Specific constructs of interest include, but are not limited to, antisense constructs to block gene expression, expression of dominant negative genetic mutations, and over-expression of the identified gene. One may also provide for expression of the identified gene or variants thereof in cells or tissues where it is not normally expressed or at abnormal times of development. Furthermore, by providing expression of a protein in cells in which it is otherwise not normally produced, one can induce changes in cellular behavior.

Protein molecules may be assayed to investigate structure/function parameters. For example, by providing for the production of large amounts of a protein product of an identified gene, one can identify ligands or substrates that bind to, modulate or mimic the action of that protein product. Drug screening identifies agents that provide, e.g., a replacement or enhancement for protein function in affected cells or for agents that modulate or negate protein function. The term "agent" as used herein describes any molecule, e.g. nucleic acid, protein or small molecule, with the capability of altering or mimicking the physiological function of an identified gene, gene regulatory region or gene product. Generally a plurality of assays is run in parallel with different agent concentrations to obtain a differential response to the various concentrations. Typically, one of these concentrations serves as a negative control, e.g., at zero concentration or below the level of detection.

A wide variety of assays may be used for this purpose, including labeled in vitro protein-protein binding assays, protein-DNA binding assays, electrophoretic mobility shift assays, immunoassays for protein binding, and the like. Also, all or a fragment of the purified protein may also be used for determination of three-dimensional crystal structure, which can be used for modeling intermolecular interactions, membrane fusion, etc.

Candidate agents encompass numerous chemical classes, though typically they are organic molecules, preferably small organic molecules, having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, and frequently at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, benzodiazapines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc may be used.

Agents, including any other compound or molecule disclosed, may be combined with a pharmaceutically acceptable carrier. Pharmaceutical carreirs include, for example, any and all solvents, dispersion media, coatings, antioxidant, isotonic and absorption delaying agents and the like. The use of such carriers and agents in pharmaceutical compounds is well known in the art. Except insofar as any conventional carrier or agent is incompatible with the active ingredient, its use in the therapeutic compositions and methods described herein is contemplated. Supplementary active ingredients can also be incorporated into the pharmaceutical compounds disclosed.

Formulation of pharmaceutical compounds may be prepared for use in various methods for administration. The formulation may be given orally, by inhalation, or may be injected, e.g. intravascular, intratumor, subcutaneous, intraperitoneal, intramuscular, etc. The dosage of the therapeutic formulation will vary widely, depending upon the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. In some cases, oral administration will require a higher dose than if administered intravenously. Identified agents of the invention can be incorporated into a variety of formulations for therapeutic administration. More particularly, the complexes can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the agents can be achieved in various ways. Agents may be systemic after administration or may be localized by the use of an implant that acts to retain the active dose at the site of implantation.

For oral preparations, an agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Additionally, agents may be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Further, agents may be utilized in aerosol formulation to be administered via inhalation. The compounds of the present invention can be formulated into pressurized acceptable propellants such as dichlorodifluoromethane, propane, nitrogen and the like. Furthermore, agents may be made into suppositories by mixing with a variety of bases such as emulsifying bases or water-soluble bases. Alternatively, identified agents of the present invention can be administered rectally via a suppository. The suppository can include vehicles such as cocoa butter, carbowaxes and polyethylene glycols, which melt at body temperature, yet are solid at room temperature.

Implants for sustained release formulations are well known in the art. Implants are formulated as microspheres, slabs, etc. with biodegradable or non-biodegradable polymers. For example, polymers of lactic acid and/or glycolic acid form an erodible polymer that is well tolerated by the host. The implant containing identified agents of the present invention may be placed in proximity to the site of action, so that the local concentration of active agent is increased relative to the rest of the body. Unit dosage forms for oral or rectal administration such as syrups, elixirs, and suspensions may be provided wherein each dosage unit, for example, teaspoonful, tablespoonful, gel capsule, tablet or suppository, contains a predetermined amount of the compositions of the present invention. Similarly, unit dosage forms for injection or intravenous administration may comprise the compound of the present invention in a composition as a solution in sterile water, normal saline or another pharmaceutically acceptable carrier. The specifications for the novel unit dosage forms of the present invention depend on the particular compound employed and the effect to be achieved, and the pharmacodynamics associated with each active agent in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

A therapeutic dose of an identified agent is administered to a host suffering from a disease or disorder. Administration may be topical, localized or systemic, depending on the specific disease. The compounds are administered at an effective dosage that over a suitable period of time substantially arrests the disease progression. It is contemplated that the composition will be obtained and used under the guidance of a physician for in vivo use.

The dose will vary depending on the specific agent and formulation utilized, type of disorder, patient status, etc., at a dose sufficient to address the disease or symptoms thereof, while minimizing side effects. Treatment may be for short periods of time, e.g., after trauma, or for extended periods of time, e.g., in the prevention or treatment of schizophrenia.

In addition or in the alternative, at steps 168 and 268, the phenotypic trait of drug response is used to stratify, or segregate, patients into various groups. The groups may be, for example, those that respond to a drug versus those that do not respond, those that respond to a drug without toxic effects, versus those that are observed to have toxic effects. At steps 170 and 270, the therapeutic may be marketed with an associated diagnostic that is capable of segregating those that will respond in an acceptable manner to the drug from those that do not. In a preferable embodiment, the rights to such drugs or other products are acquired in step 197 or 297, preferably prior to demonstration of ability to genetically stratify patients. Those rights, as well as the value-added genetic information on how to stratify patients, can then be licensed to a third-party for milestone payments and/or royalties. The drug or other products (with or without the related diagnostic kit) can also be commercialized independently or with partner(s) in order to generate product sales.

According to one aspect of the invention herein, the technology platform used for one or more of the scanning steps 120, 201, 257, 263, 265 and/or the correlation steps 150, 152, 260, 263, 265 and 269 are made available at a low or discounted price to the organization conducting the research discussed herein, preferably exclusively for at least a period of time in a specified field. In return the technology provider receives from the business organization discussed herein one or more of equity, royalties on discoveries, licenses to the content generated in one or more of steps 120, 150, 152, 260, 263, 265 and 269 in a selected field and/or improvements to the technology platform, such as improvements made to chip technology. In an alternative embodiment, the organization conducting the research discussed herein is formed as a "tracking stock" of the technology provider. In preferred embodiments, the technology provider does not maintain control (as defined by the relevant accounting standard) of the organization performing the business methods elsewhere discussed herein. In this aspect of the invention, the early financial losses of the research organization need not be consolidated with the technology provider.

What is claimed is:

1. A business method comprising:
   a. scanning human genome for single nucleotide polymorphisms across more than 10,000,000 bases;
   b. grouping said single nucleotide polymorphisms into haplotype blocks;
   c. using said haplotype blocks in association study, said association study statistically correlating at least one of said haplotype blocks with a phenotypic state;
   d. using results from step c to identify one or more therapeutic or diagnostic products; and
   e. collaboratively or independently, marketing said therapeutic or diagnostic products.

2. A business method comprising:
   a. scanning the human genome for common single nucleotide polymorphisms, said common single nucleotide polymorphisms appearing in at least 10% of all human samples, across more than 10,000,000 bases;
   b. grouping said common single nucleotide polymorphisms into haplotype blocks; and
   c. collaboratively with a partner, using said haplotype blocks in an association study, said association study statistically correlating at least one of said haplotype blocks with a phenotypic state.

3. The methods as recited in claim 1 or 2 wherein said scanning step scans genic and non-genic regions of sequences in a database, wherein genic regions include open reading frame sequences encoding specific polypeptides, intronic regions, and 5' and 3' non-coding sequences involved in regulation of gene expression that are up to 10 kB from a coding region.

4. The methods as recited in claim 1 or 2 wherein said scanning step scans more than 50,000,000 bases.

5. The methods as recited in claim 1 or 2 wherein said scanning step scans more than 100,000,000 bases.

6. The methods as recited in claim 1 or 2 wherein said scanning step scans more than 500,000,000 bases.

7. The methods as recited in claim 1 or 2 wherein said scanning step scans more than 1,000,000,000 bases.

8. The methods as recited in claim 1 or 2 wherein only single nucleotide polymorphisms that occur in more than 2% of a sample population studied are used in the grouping step.

9. The methods as recited in claim 1 or 2 wherein only single nucleotide polymorphisms that occur in more than 4% of a sample population studied are used in the grouping step.

10. The methods as recited in claim 1 or 2 wherein only single nucleotide polymorphisms that occur in more than 6% of a sample population studied are used in the grouping step.

11. The methods as recited in claim 1 or 2 wherein only single nucleotide polymorphisms that occur in more than 8% of a sample population studied are used in the grouping step.

12. The methods as recited in claim 1 or 2 wherein only single nucleotide polymorphisms that occur in more than 10% of a sample population studied are used in the grouping step.

13. The method as recited in claim 1 or 2 wherein said phenotypic state is a disease state.

14. The method as recited in claim 1 or 2 wherein said step of using said haplotype blocks in an association study comprises scanning for at least some of said single nucleotide polymorphisms in said haplotype blocks on a nucleic acid array.

15. The method as recited in claim 1 or 2 wherein said step of using said haplotype blocks in an association study comprises scanning for at least some of said single nucleotide polymorphisms in said haplotype blocks using an assay to identify single nucleotide polymorphisms.

16. The method as recited in claim 1 or 2 wherein said phenotypic state is a drug response state.

17. The method as recited in claim 1 or 2 wherein only common single nucleotide polymorphisms appearing in at least 10% of all human samples are used in said grouping step.

18. The method as recited in claim 1 wherein said association study is performed with a partner.

19. The method as recited in claim 1 or 2 wherein more than 2 chromosomes are analyzed in said scanning step.

20. The method as recited in claim 1 or 2 wherein more than 5 chromosomes are analyzed in said scanning step.

21. The method as recited in claim 2 or 18 wherein said partner provides funding for said scanning and grouping steps.

22. The method as recited in claim 2 or 18 wherein said partner provides funding for said association study.

23. The method as recited in claim 1 or 2 wherein said association study evaluates more than 500 disease and control samples.

24. The method as recited in claim 1 or 2 where said association study evaluates more than 1000 disease and control samples.

25. The method as recited in claim 2 or 18 wherein said partner provides samples used in said association study.

26. The method as recited in claim 1 or 2 further comprising the step of identifying a pharmaceutical compound to treat said phenotypic state.

27. The method as recited in claim 26 further comprising the step of collecting royalties from sales of said pharmaceutical compound.

28. The method as recited in claim 1 or 2 wherein a technology provider provides discounted technology for at least one of said scanning step or said association study and receives equity in return for said discounted technology.

29. The method as recited in claim 26 wherein said pharmaceutical compound is an antisense molecule.

30. The method as recited in claim 26 wherein said pharmaceutical compound is a protein compound.

31. The method as recited in claim 26 wherein said pharmaceutical compound is an antibody.

32. The method as recited in claim 1 wherein said association study is run without a prior hypothesis of a genetic association of said phenotypic state.

33. The method as recited in claim 1 or 2 further comprising the step of licensing a database of said haplotype blocks.

34. The method as recited in claim 1 or 2 wherein said scanning step uses a technology platform from a technology provider, said technology provider providing said technology platform at a discounted price in return for rights to improvements to said technology platform.

35. The method as recited in claim 26 wherein a partner pays royalties on said compounds.

36. The method as recited in claim 1 or 2 wherein said scanning step scans haploid genomes.

37. The method as recited in claim 1 or 2 wherein said scanning step is repeated using results of said association study to identify further said single nucleotide polymorphisms in a region of interest.

38. The method as recited in claim 25 wherein said association study is run without a prior hypothesis of a genetic association of said phenotypic state.

39. A business method comprising:
   a. individually scanning a plurality of genomes to identify common variants;
   b. pooling samples of case and control DNAs to form pooled DNAs;
   c. identifying a relative allele frequency of said common variants in said pooled DNAs to identify variants more common in one of said case or control pooled DNAs;
   d. using said variants identified as more common in a process to identify one or more therapeutic or diagnostic products; and
   e. collaboratively or independently marketing said therapeutic or diagnostic products.

* * * * *